(12) United States Patent
Chunglo et al.

(10) Patent No.: US 12,167,795 B2
(45) Date of Patent: Dec. 17, 2024

(54) MATTRESS ASSEMBLIES INCLUDING AT LEAST ONE PANEL INCLUDING PHASE CHANGE MATERIALS

(71) Applicant: Dreamwell, Ltd., Atlanta, GA (US)

(72) Inventors: Christopher F. Chunglo, Marietta, GA (US); Michael S. DeFranks, Atlanta, GA (US)

(73) Assignee: DREAMWELL, LTD., Doraville, GA (US)

( * ) Notice: Subject to any disclaimer, the term of this patent is extended or adjusted under 35 U.S.C. 154(b) by 771 days.

(21) Appl. No.: 16/276,382

(22) Filed: Feb. 14, 2019

(65) Prior Publication Data

US 2020/0260882 A1 Aug. 20, 2020

(51) Int. Cl.
| | | |
|---|---|---|
| A47C 27/15 | (2006.01) | |
| A47C 21/04 | (2006.01) | |
| A47C 27/08 | (2006.01) | |
| A47C 27/14 | (2006.01) | |
| A47C 31/12 | (2006.01) | |

(52) U.S. Cl.
CPC ............ *A47C 27/15* (2013.01); *A47C 21/046* (2013.01); *A47C 27/148* (2013.01); *A47C 27/081* (2013.01); *A47C 31/123* (2013.01)

(58) Field of Classification Search
CPC ... A47C 21/046; A47C 27/002; A47C 27/085; A47C 27/146; A47C 27/148; A47C 27/15; B29C 70/64; B29C 44/22
USPC .................................................. 5/655.9, 740
See application file for complete search history.

(56) References Cited

U.S. PATENT DOCUMENTS

| | | | |
|---|---|---|---|
| 5,837,002 A | 11/1998 | Augustine et al. | |
| 7,690,096 B1 | 4/2010 | Gladney et al. | |
| 7,793,372 B2* | 9/2010 | Lean | B29C 70/64 |
| | | | 5/655.9 |
| 2010/0263128 A1* | 10/2010 | Lean | B29C 44/22 |
| | | | 5/636 |
| 2012/0023664 A1 | 2/2012 | Joo et al. | |
| 2014/0033441 A1* | 2/2014 | Morgan | A47C 21/044 |
| | | | 5/724 |
| 2015/0067967 A1* | 3/2015 | Tyree | A47C 27/144 |
| | | | 5/691 |
| 2017/0020299 A1* | 1/2017 | Valenta | A47C 27/002 |
| 2017/0088990 A1* | 3/2017 | Schiller | A47C 27/14 |
| 2018/0049914 A1* | 2/2018 | Stewart | A61F 7/02 |
| 2019/0053634 A1* | 2/2019 | Chirackal | D01F 6/46 |

FOREIGN PATENT DOCUMENTS

CN 107242931 A 10/2017

OTHER PUBLICATIONS

International Preliminary Report on Patentability for Application No. PCT/US2020/018055 mailed May 31, 2021, 7 pages.

(Continued)

*Primary Examiner* — David R Hare
(74) *Attorney, Agent, or Firm* — CANTOR COLBURN LLP

(57) ABSTRACT

Mattress assemblies including at least one panel or layer including a preformed capsulate sheet including a plurality of cells, and a phase change material within at least a portion of the cells.

50 Claims, 2 Drawing Sheets

(56) References Cited

OTHER PUBLICATIONS

Anonymous: "Micro PCM Phase Change Material/Phase Change Fabric for Thermal Mangement Solutions", Dec. 4, 2017, XP055700760; Retrieved from the Internet: URL: https://www.andores.com/sale-9471039-micro-pcm-phase-change-material-phase-change-fabric-for-thermal-management-solutions.httml. [retrieved on Jun. 3, 2020]. Accessed online Aug. 24, 2020.

McLaggan, et al., "Flammability assessment of phase change material wall lining and insulation materials with different weight fractions," Energy and Buildings 153 (2017) 439-447; 9 pages.

Notification of Transmittal of The International Search Report and The Written Opinion of The International Searching Authority, or The Declaration, issued in International Application No. PCT/US2020/018055, mailed Aug. 6, 2020; 19 pages.

Gao, et al. Prediction of Phase Change Material (PCM) Degradation: ASHARE 2013:Thermal Performance of the Exterior Envelopes of Whole Buildings XII International Conference, pp. 1-9.

Global Advanced Phase Change Material (PCM) Market Analysis & Trends: Industry Forecast to 2025. Advanced PCM Market Report (2017); pp. 1-222.

Jeffrey S. Lauck, Evaluation of Phase Change Materials for Cooling in a Super-Insulated Passive House: Portland State University PDX Scholar, Summer Oct. 3, 2013; 70 pages total.

Ora, et al., Review on phase change change materials (PCMs) for cold thermal energy storage applications: Applied Energy 99 (2012); pp. 513-533.

Written Opinion of the International Preliminary Examining Authority for International Patent Application No. PCT/US2020/018055 mailed Feb. 25, 2021, 17 pages.

\* cited by examiner

MATTRESS ASSEMBLIES INCLUDING AT LEAST ONE PANEL INCLUDING PHASE CHANGE MATERIALS

BACKGROUND

The present disclosure generally relates to mattress assemblies including at least one panel and/or layer including phase change materials.

Phase change is a term used to describe a reversible process in which a solid turns into a liquid or a gas. The process of phase change from a solid to a liquid requires energy to be absorbed by the solid. When a phase change material ("PCM") liquefies, energy is absorbed from the immediate environment as it changes from the solid to the liquid. In contrast to a sensible heat storage material, which absorbs and releases energy essentially uniformly over a broad temperature range, a phase change material absorbs and releases a large quantity of energy in the vicinity of its melting/freezing point. Therefore, a PCM that melts below body temperature would feel cool as it absorbs heat, for example, from a body. Phase change materials, therefore, include materials that liquefy (melt) to absorb heat and solidify (freeze) to release heat. The melting and freezing of the material typically take place over a narrow temperature range.

PCMs have been used in various applications ranging from household insulation to clothing. Dispersal in preformed foams is expensive, involves an additional step after formation of the foam, and typically does not uniformly distribute the PCMs throughout foams greater than one inch in thickness. In these types of applications, the PCM is microencapsulated. Typically, the PCM material itself is a relatively inexpensive long chain hydrocarbon that is subsequently microencapsulated. Exemplary long chain hydrocarbons include octadecane, nonadecane, icosane, heptadecane, and the like. These materials have low melting point temperatures. However, as noted above, the microencapsulation process dramatically increases the price of the PCM. As one decreases the overall size of the microencapsulated PCM, the net volume of the PCM within the microencapsulated PCM significantly decreases whereas the volume taken up by the capsule increases.

BRIEF SUMMARY

Disclosed herein are mattress assemblies including at least one panel of including a phase change material. In one or more embodiments, the mattress assembly includes at least one layer proximate to a sleeping surface of the mattress assembly spanning at least a portion of the length and/or width of the sleeping surface including a two-ply preformed capsulate sheet comprising a plurality of cells; and a phase change material within at least a portion of the plurality of cells.

In one or more embodiments, the mattress assembly includes a core layer; at least one layer overlaying the core layer including a two-ply preformed capsulate sheet including a plurality of cells, and a phase change material within at least a portion of the plurality of cells; and a foam layer overlaying the at least one layer, wherein the at least one layer and the foam layer are proximate to a sleeping surface of the mattress assembly.

In one or more embodiments, the mattress assembly includes a first layer proximate to a sleeping surface of the mattress assembly spanning at least a portion of the length and/or width of the sleeping surface including a two-ply preformed capsulate sheet including a plurality of cells, and a phase change material within at least a portion of the plurality of cells, wherein the phase change layer in the first layer has a first transition temperature; and at least one additional layer underlying the first layer, the at least one additional layer spanning at least a portion of the length and/or width of the sleeping surface comprises a two-ply preformed capsulate sheet including a plurality of cells; and a phase change material within at least a portion of the plurality of cells, wherein the phase change layer in the at least one additional layer has a transition temperature different from the first transition temperature of the first layer.

The disclosure may be understood more readily by reference to the following detailed description of the various features of the disclosure and the examples included therein.

BRIEF DESCRIPTION OF THE DRAWINGS

Referring now to the figures wherein the like elements are numbered alike.

DETAILED DESCRIPTION

Figure 1:
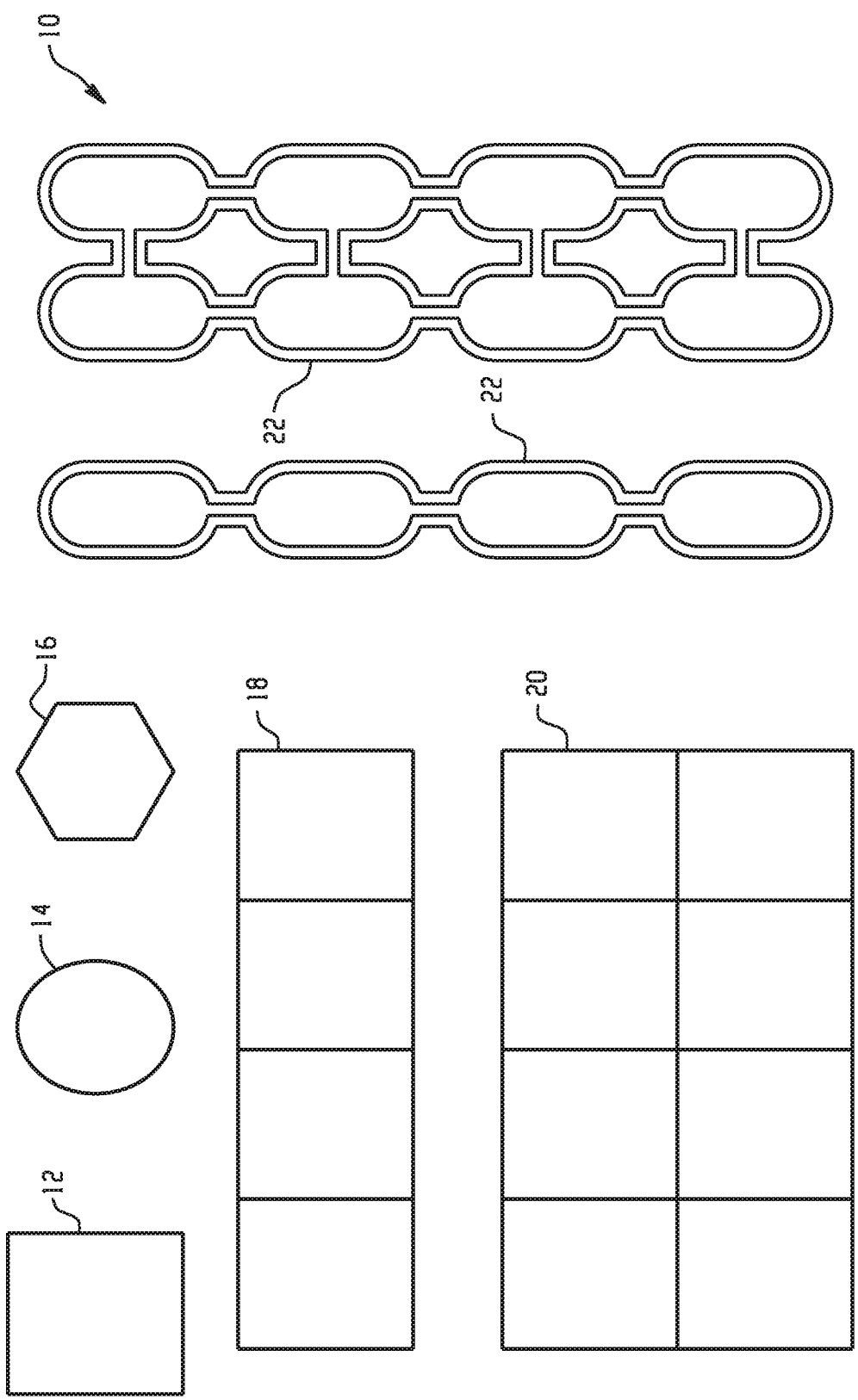
FIG. 1 illustrates top down views of exemplary cell configurations in accordance with an embodiment of the present disclosure.

Disclosed herein are mattresses including at least one panel or layer including phase change materials encapsulated with a preformed capsulate sheet similar to so-called bubble wrap including individual cells and/or interconnected cells that can be filled with the desired phase change material or mixture of phase change materials. The preformed capsulate sheets are formed of materials selected to have mechanical properties sufficient to accommodate volume changes that may occur during phase change transitions, withstand the rigors of product durability, and maintain thermal and tactile comfort during use in a variety of end use environments. At least one panel or layer including the phase change materials can be used as a topper layer and/or as one or more of the layers defining the mattress. In one or more embodiments, at least one panel or layer including the encapsulated phase change materials is at or proximate to a sleeping surface and may span the length and/or width of the sleeping surface or a portion thereof to define one or more zones. The multiple zones of the phase change material can be the same or different phase change material, can have different amounts of the phase change material depending on location one the sleeping surface, and/or can include different cell configurations of the preformed capsulate sheet.

Phase change materials are relatively inexpensive whereas the cost to manufacture and encapsulate prior art microencapsulated phase change materials are relatively high since the encapsulate material has a high surface area relative to the amount of phase change material contained within each cell. As will be described in greater detail below, the preformed capsulate sheets of the present invention provide a markedly higher volume of phase change material to be encapsulated that lowers the surface area of the encapsulate material relative to the amount of phase change material, thereby providing a significant cost reduction. In this manner, instead of milligrams to grams of phase change material within a given layer as is currently done in the prior art, the present invention provides the capability of utilizing hundreds of grams or pounds of phase change material within a given layer as may be desired for different applications. The increased amount of phase change material within a given layer can be configured to extend the effective solid to liquid or liquid to solid transition time of the phase change material throughout an entire sleep cycle of 8 hours or more, which is unlike prior art microencapsulated phase change layers that generally provide an effective transition time of a few minutes to about 30 minutes. As used herein, the term "transition time" generally refers to the time of the transition of the phase change material per unit cell volume of the phase change material during use by an end user on the mattress. For example, an end user would feel cool as the phase change material absorbs heat from the end user during the sleep cycle. In the present disclosure, the amount of phase change material within a given cell can be calculated to provide cooling or heating from about 30 minutes to about 8 hours or longer.

Referring now to FIG. 1, there is shown various non-limiting shapes of an exemplary cell included in the preformed capsulate sheet. The cells within the sheet can have the same or different shape and/or size. Moreover, the cells can be individual cells or linked cells, wherein the linked cells may have a fluid connection therebetween and/or at least one shared wall. As shown in FIG. 1, the exemplary individual cells 10 can have any geometric shape such as the illustrated square shape 12, circular shape 14, or hexagonal shape 16. Further illustrated are linear linked cells 18, multi-linked cells 20, and fluidly interconnected channels 22 connecting different cells that allow the flow of PCM material between the cells. In the case of individual cells, the cellular volumes are generally greater than 1 cm$^3$.

Figure 2:
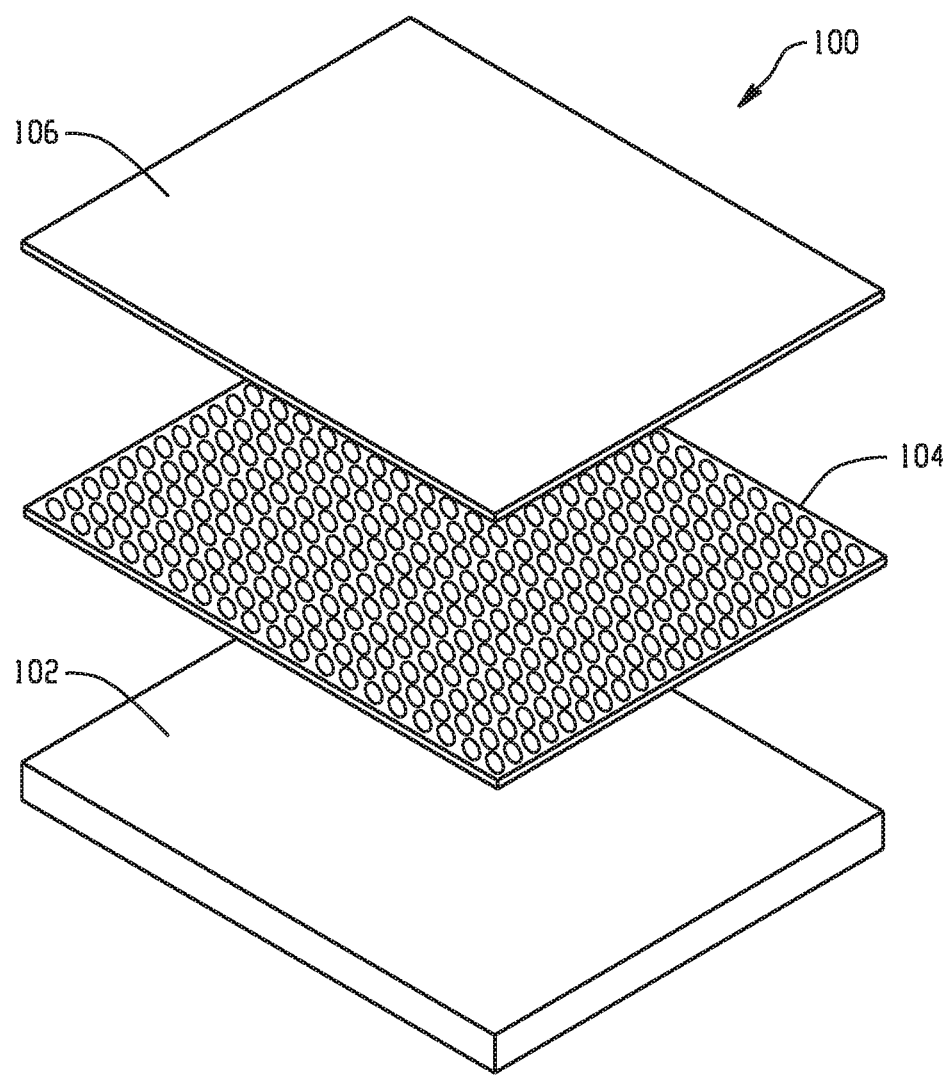
FIG. 2 illustrates an exploded perspective view of a mattress assembly including a phase change capsulate sheet layer in accordance with an embodiment of the present disclosure.

FIG. 2 shows an exploded perspective view of an exemplary mattress assembly including a phase change capsulate sheet layer as described above. The mattress assembly 100 includes a base core layer 102 configured with generally planar top and bottom surfaces but may include surfaces that are not flat such as convoluted foams. For this as well as the other embodiments disclosed herein, the core layer 102 is chosen to have a thickness less than or about equal to the overall thickness of the mattress assembly. Generally, the thickness of the core layer 102 is within a range of 4 inches to 10 inches, with a range of about 6 inches to 8 inches thickness in other embodiments, and a range of about 6 to 6.5 inches in still other embodiments.

The core layer 102 can be formed of open or closed cell foam including, without limitation, viscoelastic foams, non-viscoelastic foams, latex foams, polyurethane foams, and the like. In one embodiment, the core layer 102 is pre-stressed foam layer. That is, the foam core layer is subjected to a pre-stressing process such as disclosed in U.S. Pat. No. 7,690,096 to Gladney et al., incorporated herein by reference in its entirety. By way of example, a force can applied to at least a section of the foam core layer in an amount sufficient to temporarily compress its height so as to permanently alter a mechanical property of the foam layer to provide a pre-stressed foam layer having a firmness that is different from the firmness of a similar foam that was not pre-stressed.

The foam core layer 102 has a density of 1 pound per cubic foot (lb/ft$^3$) to 6 lb/ft$^3$. In other embodiments, the density is 1 lb/ft$^3$ to 5 lb/ft$^3$ and in still other embodiments, from 1.5 lb/ft$^3$ to 4 lb/ft$^3$. By way of example, the density can be about 1.5 lb/ft$^3$. The hardness of the foam core layer, also referred to as the indention load deflection (ILD) or indention force deflection (IFD), is within a range of 20 to 45 pounds-force, wherein the hardness is measured in accordance with ASTM D-3574 and is generally defined as the amount of force in pounds required to indent a 8" disc into a 15"×15"×4" foam sample and make a 1" indentation. In other embodiments, the hardness is about 20 to 30 pounds-force.

Alternately, the core layer 102 could be constructed of an innerspring assembly, an air bladder, an air/foam bladder or bladder filled with any fluid. The coil springs of the innerspring assembly may be open coils or may be encased coils, e.g., pocketed (Marshall) coils. In some embodiments, the coil spring layer may further include foam. Bordering the outer row of the coil springs in the innerspring assembly is a side rail (not shown) made, for example, of foam or another suitable material known to those skilled in the art. With regard to the bladder, the core layer 102 may further include foam rail encasement around the bladders and may also include foam layers consisting of open or closed cell foam including, without limitation, viscoelastic foams, non-viscoelastic foams, latex foams, polyurethane foams, and the like place above or below the bladders.

Phase change preformed capsulate layer 104 overlays the core layer 102 and is positioned proximate to a sleeping surface. Advantageously, the phase change provides extended cooling as needed to an end user of the mattress assembly. The phase change layer 104 generally has a thickness equal to or less than 2 inches in some embodiments, a thickness equal to or less than 1 inch in other embodiments, or a thickness equal to or less than 0.5 inches in still other embodiments. In other embodiments, the thickness is greater than or equal to 0.5 inch. In one or more embodiments, the amount of phase change material in the preformed capsulate layer 104 is at least 100 grams per square foot of surface area, greater than about 200 grams per square foot in other embodiments, and greater than about 454 grams per square foot in still other embodiments.

Figure 3:
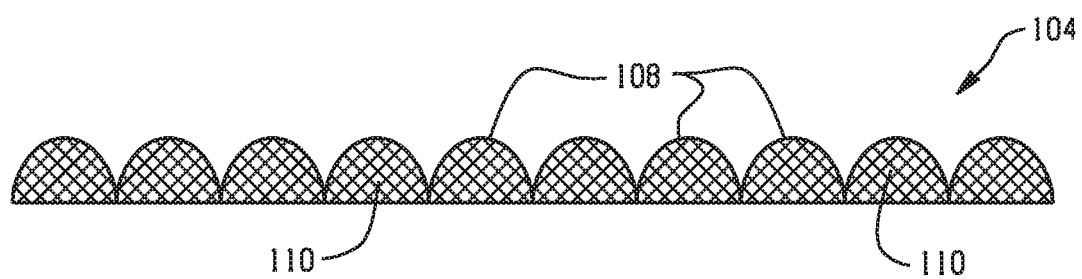
FIG. 3 illustrates a cross sectional view of an exemplary phase change capsulate sheet layer in accordance with an embodiment of the present disclosure.

As shown more clearly in FIG. 3, the phase change capsulate sheet layer 104 includes a plurality of cells 108 formed of a flexible material such as polyethylene. The cells are filled with a phase change material 110 or a mixture of phase change materials. Still further, additional material(s) such as flame retardants, antibacterial agents, thermally conductive components, and/or the like can be included in the cells. The phase change layer 104 has a generally planar top and bottom surface and is intended to be sandwiched between layers as is generally shown in FIG. 2. Although the phase change layer is shown spanning the width and length of the mattress assembly, it should be apparent that phase change layer can be configured to span a portion of the mattress assembly so as to provide one or more different zones. By way of example, which is not intended to be limiting, a phase change layer 104 configured for use in queen sized mattress can have a width of 59.5 inches and a length of 79.5 or span a portion thereof.

In one or more embodiments, the capsulate sheet layer 104 can contain channels or interconnected cells that have been filled with an open cell foam or other permeable materials. This foam is then saturated with the PCM while it is in a liquid state and then sealed. This would help the layer keep its shape when the PCM changes to its liquid state. Without the addition of the foam when the PCM changes state to a liquid it would naturally migrate to the side under the pressure of the body. The addition of the foam will insure there is still a level of support being provided by the layer even after the PCM transition to a liquid state.

The particular configuration in terms of cell shape, cell size, cell spatial volume, spacing between cells, fluid connection between linked cells, and the like of the phase change capsulate sheet layer 104 is not intended to be limited. Generally, as it relates to the size, spatial volume, and shape of the cell, the amount of phase change material contained therein is effective to provide a phase transition time to the end user of at least about 30 minutes or greater. In contrast, prior art microencapsulated phase change materials for bedding applications are generally on the order of a few micrograms per square foot.

By way of example, heat production of an end user can be about 60 Watts/square meter, which is equivalent to about 19 BTU/hour-square foot. The effective surface area of an exemplary individual torso in its entirety is about 4 square feet. As such, the effective surface area of the individual torso when prone and in contact with a sleeping surface of a mattress, e.g., an end user lying on his back, is about half, i.e., 2 square feet. Accordingly, the end user would generate about 38 BTU/hour (i.e., 19 BTU/hours-square foot×2 square feet=38 BTU/hour). If the latent heat of a phase change material is 100 BTU/pound, then the amount of phase change material needed to provide effective cooling during a sleep cycle of about 8 hours would be about 0.4 pounds per hour (38 BTU/hour/100 BTU/pounds=about 0.4 pounds per hour). As such, the total amount of phase change material in this example to provide heat dissipation during an 8 hour sleep cycle would be about 3.2 pounds (8×0.4 pounds/hour). Prior art microencapsulated phase change materials typically are on the order milligrams per square foot, not grams or pounds, and because of the relatively small amount of phase change material present in prior art microencapsulated phase change materials, the transition duration is relatively short, i.e., the transition from solid to liquid is on the order of about 15 to 30 minutes.

Referring back to FIG. 2, a cover panel 106 is shown disposed on the phase change layer 104. The cover panel layer can be formed from viscoelastic foam or non-viscoelastic foam depending on the intended application. The foam itself can be of any open or closed cell foam material including without limitation, latex foams, natural latex foams, polyurethane foams, combinations thereof, and the like. The cover panel 106 has planar top and bottom surfaces. The thickness of the cover panel is generally within a range of about 0.5 to 2 inches in some embodiments, and less than 1" in other embodiments so as to provide the extended cooling benefits of the underlying phase change layer 104. The density of the cover panel layer 106 can be within a range of 1 to 8 lb/ft$^3$ in some embodiments, and 2 to 4 lb/ft$^3$ in other embodiments. The hardness is within a range of about 7 to 22 pounds-force in some embodiments, and less than 15 pounds-force in other embodiments. In one or more embodiments, the cover panel can be configured as a quilt panel or a convoluted foam.

The various multiple stacked mattress layers 102, 104, and 106 may be adjoined to one another using an adhesive or may be thermally bonded to one another or may be mechanically fastened to one another as may be desired for different applications.

The mattress assembly 100 can further include a side rail assembly (not shown) about all or a portion of the perimeter of the mattress assembly defined by foam layers 102, 104, 106. The side rails that define the assembly may be attached to or placed adjacent to at least a portion of the perimeter of the stacked mattress layers 102, 104, 106, and may include metal springs, spring coils, encased spring coils, foam, latex, natural latex, latex w/gel, gel, viscoelastic gel, fluid bladders, or a combination thereof, in one or more layers. The side rails may be placed on one or more of the sides of the stacked mattress layers, e.g., on all four sides of the stacked mattress layers, on opposing sides, on three adjacent sides, or only on one side of the stacked mattress layers. In certain embodiments, the side rails may comprise edge supports with a firmness greater than that provided by the stacked mattress layers. The side rails may be fastened to the stacked mattress layers via adhesives, thermal bonding, or mechanical fasteners.

For ease in manufacturing the mattress assembly, the side rail assembly may be assembled in linear sections that are joined to one another to form the perimeter about the mattress layers. Alternatively, the ends may be mitered or have some other shape, e.g., lock and key type shape.

In one or more embodiments, the at least one panel of phase change material is disposed under the fabric cover or quilt panel of the mattress as described above, which is typically one of the uppermost layers of a mattress. Optionally, the at least one panel of the phase change material can be a removable topper layer. In these embodiments, high conductivity foams can be placed above and/or below the phase change material layer 104 to enhance thermal transfer. Advantageously, selective positioning of the phase change materials with or without the high conductivity foam layers above and/or below the phase change material layer as noted above can influence the rate of phase change, e.g., phase change from a liquid state back to a solid state after the end user has left the mattress.

In one or more embodiments, multiple panels of the phase change material are disposed under the fabric cover or quilt panel of the mattress as described above, wherein each panel has a different transition temperature. For example, the multiple panels can be arranged to provide a gradient. The panel nearest the sleeper, i.e., the first panel, could have a higher trigger temperature than a lower panel, i.e., the second panel, underlying the first panel. This could help extend the affective time the PCM could help remove excessive heat.

The preformed capsulate can be in the form of a bubble wrap. The bubble wrap can include a plurality of cells of any configuration and can be filled and sealed at the point of use. For example, the desired phase change material or phase change materials can be heated above its melting point and injected into one or more of the cells and subsequently sealed. Generally, the capsulate sheets are two-ply and are formed of a resilient material such as polyethylene to prevent hard spots when in use and is selected to be compatible with the intended PCM material(s) to be used. As used herein, the term "two-ply" generally refers to two separate sheets, first and second sheets, that are coupled to one another to form the capsulate sheet as described in greater detail below. The individual sheets themselves that define the two-ply capsulate sheet configuration can be formed from a single layer or multiple layers as may be desired for desired strength and resiliency. Moreover, each cell should be configured to accommodate any volume changes related to the phase change of the PCM material(s).

Phase change materials that can be incorporated in the preformed capsulate in accordance with various embodiments of the invention include a variety of organic and inorganic substances including paraffins; bio-phase change materials derived from acids, alcohols, amines, esters, and the like; salt hydrates; and the like. The particular phase change material or mixtures thereof are not intended to be limited.

Exemplary phase change materials include hydrocarbons (e.g., straight chain alkanes or paraffinic hydrocarbons, branched-chain alkanes, unsaturated hydrocarbons, halogenated hydrocarbons, and alicyclic hydrocarbons), bio-phase change materials derived from fatty acids and their derivatives, (e.g., alcohols, amines, esters, and the like), hydrated salts (e.g., calcium chloride hexahydrate, calcium bromide hexahydrate, magnesium nitrate hexahydrate, lithium nitrate trihydrate, potassium fluoride tetrahydrate, ammonium alum, magnesium chloride hexahydrate, sodium carbonate decahydrate, disodium phosphate dodecahydrate, sodium sulfate decahydrate, and sodium acetate trihydrate), waxes, oils, water, fatty acids, fatty acid esters, dibasic acids, dibasic esters, 1-halides, primary alcohols, aromatic compounds, clathrates, semi-clathrates, gas clathrates, anhydrides (e.g., stearic anhydride), ethylene carbonate, polyhydric alcohols (e.g., 2,2-dimethyl-1,3-propanediol, 2-hydroxymethyl-2-methyl-1,3-propanediol, ethylene glycol, polyethylene glycol, pentaerythritol, dipentaerythritol, pentaglycerine, tetramethylol ethane, neopentyl glycol, tetramethylol propane, 2-amino-2-methyl-1,3-propanediol, monoaminopentaerythritol, diaminopentaerythritol, and tris (hydroxymethyl)acetic acid), polymers (e.g., polyethylene, polyethylene glycol, polyethylene oxide, polypropylene, polypropylene glycol, polytetramethylene glycol, polypropylene malonate, polyneopentyl glycol sebacate, polypentane glutarate, polyvinyl myristate, polyvinyl stearate, polyvinyl laurate, polyhexadecyl methacrylate, polyoctadecyl methacrylate, polyesters produced by polycondensation of glycols (or their derivatives) with diacids (or their derivatives), and copolymers, such as polyacrylate or poly(meth)acrylate with alkyl hydrocarbon side chain or with polyethylene glycol side chain and copolymers comprising polyethylene, polyethylene glycol, polyethylene oxide, polypropylene, polypropylene glycol, or polytetramethylene glycol), metals, and mixtures thereof. Bio-phase change materials have high latent heat, small volume change for phase transition, sharp well-defined melting temperature and reproducible behavior.

The selection of a phase change material will typically be dependent upon a desired transition temperature. For example, a phase change material having a transition temperature slightly above room temperature but below skin temperature may be desirable for mattress applications to maintain a comfortable temperature for a user.

A suitable phase change material can have a phase transition temperature within a range of about 22° to about 40° C. In one or more other embodiments, the transition temperature within a range of about 26° C. to about 30° C. With regard to paraffin phase change materials, the number of carbon atoms of a paraffinic hydrocarbon typically correlates with its melting point. For example, n-octacosane, which contains twenty-eight straight chain carbon atoms per molecule, has a melting point of 61.4° C. whereas n-tridecane, which contains thirteen straight chain carbon atoms per molecule, has a melting point of −5.5° C. According to an embodiment of the invention, n-octadecane, which contains eighteen straight chain carbon atoms per molecule and has a melting point of 28.2° C., is particularly desirable for mattress applications.

Other useful phase change materials include polymeric phase change materials having transition temperatures within a range of about 22° to about 40° C. in one or more embodiments, and a transition temperature within a range of about 26° to about 30° C. in other embodiments. A polymeric phase change material may comprise a polymer (or mixture of polymers) having a variety of chain structures that include one or more types of monomer units. In particular, polymeric phase change materials may include linear polymers, branched polymers (e.g., star branched polymers, comb branched polymers, or dendritic branched polymers), or mixtures thereof. A polymeric phase change material may comprise a homopolymer, a copolymer (e.g., terpolymer, statistical copolymer, random copolymer, alternating copolymer, periodic copolymer, block copolymer, radial copolymer, or graft copolymer), or a mixture thereof. As one of ordinary skill in the art will understand, the reactivity and functionality of a polymer may be altered by addition of a functional group such as, for example, amine, amide, carboxyl, hydroxyl, ester, ether, epoxide, anhydride, isocyanate, silane, ketone, and aldehyde. Also, a polymer comprising a polymeric phase change material may be capable of crosslinking, entanglement, or hydrogen bonding to increase its toughness or its resistance to heat, moisture, or chemicals.

According to some embodiments of the invention, a polymeric phase change material may be desirable as a result of having a higher molecular weight, larger molecular size, or higher viscosity relative to non-polymeric phase change materials (e.g., paraffinic hydrocarbons). In addition to providing thermal regulating properties, a polymeric phase change material may provide improved mechanical properties (e.g., ductility, tensile strength, and hardness).

For example, polyethylene glycols may be used as the phase change material in some embodiments of the invention. The number average molecular weight of a polyethylene glycol typically correlates with its melting point. For instance, a polyethylene glycol having a number average molecular weight range of 570 to 630 (e.g., Carbowax 600) will have a melting point of 20° to 25° C., making it desirable for mattress applications. Further desirable phase change materials include polyesters having a melting point in the range of 22° to 40° C. that may be formed, for example, by polycondensation of glycols (or their derivatives) with diacids (or their derivatives).

According to some embodiments of the invention, a polymeric phase change material having a desired transition temperature may be formed by reacting a phase change material (e.g., an exemplary phase change material discussed above) with a polymer (or mixture of polymers). Thus, for example, n-octadecylic acid (i.e., stearic acid) may be reacted or esterified with polyvinyl alcohol to yield polyvinyl stearate, or dodecanoic acid (i.e., lauric acid) may be reacted or esterified with polyvinyl alcohol to yield polyvinyl laurate. Various combinations of phase change materials (e.g., phase change materials with one or more functional groups such as amine, carboxyl, hydroxyl, epoxy, silane, sulfuric, and so forth) and polymers may be reacted to yield polymeric phase change materials having desired transition temperatures.

Table 1 provides a list of exemplary commercially available phase change materials and the corresponding metal point (Tm) suitable for use in mattress applications described herein.

TABLE 1

| Material | Supplier | Type | Form | Melting point, Tm |
|---|---|---|---|---|
| 0500- Q28 BioPCM | Phase Change Energy Solutions | Functionalized BioPCM | Bulk, Macro-encapsulated | 28° C. (82° F.) |
| PureTemp 28 | PureTemp LLC | Organic | Bulk | 28° C. (82° F.) |
| RT27 | Rubitherm GmbH | Organic | Bulk | 28° C. (82° F.) |
| Climsel C28 | Climator | Inorganic | Bulk | 28° C. (82° F.) |
| RT 30 | Rubitherm GmbH | Organic | Bulk | 28° C. (82° F.) |
| RT 28 HC | Rubitherm GmbH | Organic | Bulk | 28° C. (82° F.) |
| A28 | PlusICE | Organic | Bulk | 28° C. (82° F.) |
| MPCM 28 | Microtek | Organic | Micro-encapsulated | 28° C. (82° F.) |
| MPCM 28D | Microtek | Organic | Micro-encapsulated | 28° C. (82° F.) |
| Latest 29 T | TEAP | Inorganic | Bulk | 28° C. (82° F.) |
| 0500- Q29 BioPCM | Phase Change Energy Solutions | Functionalized BioPCM | Bulk, Macro-encapsulated | 29° C. (84° F.) |
| 29 C. ° Infinite R | Insolcorp | Inorganic | Macro-encapsulated | 29° C. (84° F.) |
| savE HS 29 | Pluss | Inorganic | Bulk | 29° C. (84° F.) |
| savE OM 29 | Pluss | Organic | Bulk | 29° C. (84° F.) |
| savE FS 29 | Pluss | Organic | Bulk | 29° C. (84° F.) |
| PureTemp 29 | PureTernp LLC | Organic | Bulk | 29° C. (84° F.) |
| TH 29 | TEAP | Inorganic | Bulk | 29° C. (84° F.) |
| A29 | PlusICE | Organic | Bulk | 29° C. (84° F.) |
| PCM-HS29P | SAVENRG | inorganic | Bulk | 29° C. (84° F.) |
| CrodaTherm ™ 29 | Croda International Pic | Organic | Bulk | 29° C. (84° F.) |
| 0500- Q30 BioPCM | Phase Change Energy Solutions | Functionalized BioPCM | Bulk, Macro-encapsulated | 30° C. (86° F.) |
| S30 | PlusICE | inorganic | Bulk | 30° C. (86° F.) |
| savE OM 30 | Pluss | Organic | Bulk | 31° C. (88° F.) |
| savE FS 30 | Pluss | Organic | Bulk | 31° C. (88° F.) |
| RT 31 | Rubitherm GmbH | Organic | Bulk | 31° C. (88° F.) |
| 0500- Q32 BioPCM | Phase Change Energy Solutions | Functionalized BioPCM | Bulk, Macro-encapsulated | 32° C. (90° F.) |
| savE OM 32 | Pluss | Organic | Bulk | 32° C. (90° F.) |
| Climsel C32 | Climator | inorganic | Bulk | 32° C. (90° F.) |
| S32 | PlusICE | Inorganic | Bulk | 32° C. (90° F.) |
| A32 | PlusICE | Organic | Bulk | 32° C. (90° F.) |
| PCM-OM32P | SAVENRG | Organic | Bulk | 32° C. (90° F.) |

Also, the phase change material according to one or more embodiments can have a latent heat that is at least about 40 Joules/gram (J/g), at least about 50 J/g in other embodiments, and at least about 60 J/g in still other embodiments. As used herein, the term "latent heat" can refer to an amount of heat absorbed or released by a substance (or mixture of substances) as it undergoes a transition between two states. Thermal energy can be stored or removed from a phase change material, and the phase change material typically can be effectively recharged by a source of heat or cold. By selecting an appropriate phase change material, a multi-component fiber can be designed for use in any one of numerous products.

The phase change material can include a mixture of two or more substances (e.g., two or more of the exemplary phase change materials discussed above). By selecting two or more different substances (e.g., two different paraffinic hydrocarbons) and forming a mixture thereof, a temperature stabilizing range can be adjusted over a wide range to extend the cooling effect over a longer period of time. For example, octadecane can be used as the primary phase change material to which a small amount of phase change material(s) having a lower carbon content (e.g., $C_{16}$, $C_{17}$) can be used to lower the melting point, which can make the mixture less hard at room temperature. According to some embodiments of invention, the mixture of two or more different substances may exhibit two or more distinct transition temperatures or a single modified transition temperature.

During manufacture of the layer, the phase change material in the raw form may be provided as a solid in a variety of forms (e.g., bulk form, powders, pellets, granules, flakes, microencapsulates, and so forth) or as a liquid in a variety of forms (e.g., molten form, dissolved in a solvent, and so forth).

As noted above, the phase change material is provided in at least a portion of the cells of the preformed capsulate sheet, which generally consist of flexible pouches partially filled with air. In one or more embodiments, the phase change material can be injected directly into a cell and subsequently sealed using a hardener or a sealing adhesive. In other embodiments, recesses are formed in a carrier sheet and subsequently filled with the desired phase change material. A cover sheet is the coupled applied to the carrier sheet. The coupling can be provided with an applied adhesive or can be thermally fused. In one or more embodiments, the phase change material can be maintained above its melting temperature during the injection.

In one or more embodiments, a flame retardant can be injected into the cell in addition to the phase change material. Exemplary fire retardants include, without limitation, chlorinated flame retardant compounds, such as chlorinated hydrocarbons, chlorinated phosphate esters, chlorinated polyphosphates, chlorinated organic phosphonates, chloroalkyl phosphates, polychlorinated biphenyls, polychlorinated dibenzo-p-dioxins and dibenzofurans are molecules containing a high concentration of chlorine that generally act chemically in the gas phase. They are often used in combination with antimony trioxide and/or zinc borate as a synergist. Three main families of chlorinated compounds include: (a) chlorinated paraffins; (b) chlorinated alkyl phosphates; and (c) chlorinated cycloaliphatic compounds Examples of chlorinated compounds include dodecachlorodimethanodibe-nzocyclooctane, tris(2-chloroethyl)phosphate, tris(2-chloro-1-methylethyl)phosphate, tris(2-chloro-1-(chloromethyl)ethyl)phosphate(TDPP), tris(chloropropyl) phosphate, tris (dichloropropyl)phosphate, tris(2-chloroethyl)phosphite, ammonium chloride, chlorendic acid, chlorendic anhydride, tris(dichlorobropropyl)phosphite, Bis(hexachlorocyclopentadieno)cyclo-octane, tris(dichloropropyl)phosphite, bis [bis(2-chloroethoxy)-phosphinyl]isop-ropylchloro-ethyl phosphate and MIREX® (1,1a,2,2,3,3a,4,5,5,5a,5b,6-dodecac-hloroocta-hydro-1,3,4-metheno-1H-cyclobuta(cd)pentalene).

Brominated fire retardant compounds, such as brominated organic compounds and brominated hydrocarbons, exhibit fire retardant efficiency in many materials. The three main families of brominated fire retardants include: (a) aliphatic brominated compounds; (b) aromatic brominated compounds; and (c) brominated epoxy fire retardants. Aliphatic brominated compounds include, for example, trisbromoneopentylphosphate, trisbromoneopentyl alcohol, dibromoneopentyl glycol, hexabromocyclohexane, hexabromocyclododecane, tetrabromo cyclopentane, hexabromo cyclohexane, hexabromo cyclooctane, hexabromo cyclodecane and hexabromo cyclododecane. Aromatic brominated compounds include, for example, hexabromo benzene, decabromobiphenyl, octabromodiphenyl oxide, hexabromobenzene, tris (tribromophenyl)triazine, tetrabromobisphenolA bis (2,3 dibromo propyl ether), dibromoneopentyl glycol, poly (pentabromobenzyl acrylate), pentabromodiphenyl ether, octabromodiphenyl oxide, octabromodiphenyl ether, decabromodiphenyl, decabromodiphenyl ethane, decabromodiphenyl oxide, decabromodiphenyl ether, tetrabromobisphenol A and brominated trimethylphenyl indan. Brominated epoxy fire retardants include brominated epoxy oligomers and polymers.

Other brominated fire retardant compounds include brominated diphenyl ethers, polybrominated diphenyl ethers, dimethyl-3-(hydroxymethylamino)-3-oxopropyl phosphonate, pentabromo toluene, tetrabromo chlorotoluene, pentabromo phenol, tribromo aniline, dibromobenzoic acid, pentabromotoluene, decabromodiphenyl oxide, tribromophenol, hexabromocyclododecane, brominated phosphorous, ammonium bromide, decabromobiphenyl oxide, pentabromobiphenyl oxide, decabromobiphenyl ether, 2,3-dibromopropanol, octabromobiphenyl ether, octabromodiphenyl oxide, tetrabromobiphenyl ether, hexabromocyclododecane, bis(tetrabromophthalimido) ethane, bis (tribromophenoxy)ethane, brominated polystyrene, brominated epoxy oligomer, polypentabromobenzyl acrylate, tetrabromobisphenol compounds, dibromopropylacrylate, dibromohexachlorocyclopentadienocyclooctane, N.sup.1-ethyl(bis)dibromonon-boranedicarboximide, decabromodiphenyloxide, decabromodiphenyl, hexabromocyclohexane, hexabromocyclododecane, tetrabromo bisphenol A, tetrabrombisphenol S, N'N'-ethylbis(dibromonon-bomene)dicarboximide, hexachlorocyclopentadieno-dibromocyclooctane, tetrabromodipenta-erythrito-1, pentabromoethylbenzene, decabromodiphenyl ether, tetrabromophthalic anhydride, hexabromobiphenyl, octabromobiphenyl, pentabromophenyl benzoate, bis-(2,3-dibromo-1-propyl)phthalate, tris (2,3-dibromopropyl) phosphate, N,N'-ethylene-bis-(tetrabromophthalimide), tetrabromophthalic acid diol [2-hydroxypropyl-oxy-2-2-hydroxyethylethyl-tetrabromophthalate]-, polybrominated biphenyls, tetrabromobisphenol A, tris(2,3-dibromopropyl)phosphate, tris(2-chloroethyl)phosphite, tris(dichlorobromopropyl)phosphite, diethyl phosphite, dicyandiamide pyrophosphate, triphenyl phosphite, ammonium dimethyl phosphate, bis(2,3-dibromopropyl)phosphate, vinylbromide, polypentabromobenzyl acrylate, decabromodiphenyl oxide, pentabromodiphenyl oxide, 2,3-dibromopropanol, octabromodiphenyl oxide, polybrominated dibenzo-p-dioxins, dibenzofurans and bromo-chlorinate paraffins.

Phosphorous-based fire retardants are compounds that include phosphorous, such as halogenated phosphates (chlorinated phosphates, brominated phosphates and the like), non-halogenated phosphates, triphenyl phosphates, phosphate esters, polyols, phosphonium derivatives, phosphonates, phosphoric acid esters and phosphate esters, which are the largest class of phosphorous flame retardant compounds. Phosphorous-based fire retardants are usually composed of a phosphate core to which is bonded alkyl (generally straight chain) or aryl (aromatic ring) groups. Halogenated phosphate compounds are often introduced to decrease total halogen concentration. Non-halogenated phosphate compounds include, for example, red phosphorous, inorganic phosphates, insoluble ammonium phosphate, ammonium polyphosphate, ammonium urea polyphosphate, ammonium orthophosphate, ammonium carbonate phosphate, ammonium urea phosphate, diammonium phosphate, ammonium melamine phosphate, diethylenediamine polyphosphate, dicyandiamide polyphosphate, polyphosphate, urea phosphate, melamine pyrophosphate, melamine orthophosphate, melamine salt of boron-polyphosphate, melamine salt of dimethyl methyl phosphonate, melamine salt of dimethyl hydrogen phosphite, ammonium salt of boronpolyphosphate, urea salt of dimethyl methyl phosphonate, organophosphates, phosphonates and phosphine oxide. Phosphate esters include, for example, trialkyl derivatives, such as triethyl phosphate and trioctyl phosphate, triaryl derivatives, such as triphenyl phosphate, and aryl-alkyl derivatives, such as 2-ethylhexyl-diphenyl phosphate.

Other examples of phosphorous-based fire retardants include methylamine boron-phosphate, cyanuramide phosphate, cresyl diphenyl phosphate, tris(1-chloro-2-propyl) phosphate, tris(2-chloroethyl)phosphate, tris(2,3-dibromopropyl)phosphate, triphenyl phosphate, magnesium phosphate, tricresyl phosphate, hexachlorocyclopentadiene, isopropyl triphenyl phosphate, tricresol phosphate, ethanolamine dimethyl phosphate, cyclic phosphonate ester, monoammonium phosphate and diammonium phosphate, which permit a char formation as a result of esterification of hydroxyl groups with the phosphoric acid, trialkyl phosphates and phosphonates, such as triethyl phosphate and dimethyl, aryl phosphates, such as triaryl phosphates, isopropyl triphenyl phosphate, octylphenyl phosphate, triphenylphosphate, ammonium phosphates, such as ammonium phosphate, ammonium polyphosphate and potassium ammonium phosphate, cyanuramide phosphate, aniline phosphate, trimethylphosphoramide, tris(1-aziridinyl)phosphine oxide, triethylphosphate, Bis(5,5-dimethyl-2-thiono-1,3,2-dioxaphosphorinamyl)oxide, Bis(2-chloroethyl)vinyl phosphate, dimethylphosphono-N-hydroxyme-thyl-3-propionamide, tris(chloropropyl)phosphate, tris(2-butoxyethyl) phosphate, tris (2-chloroethyl) phosphate, tris(2-ethylhexyl) phosphate, tris(chloropropyl)phosphate, tetrakis (hydroxymethyl)phosphonium salts, such as tetrakis (hydroxymethyl) phosphonium chloride and tetrakis (hydroxymethyl)phosphonium sulfate, n-hydroxymethyl-3-(dimethylphosphono-)-propionamide, urea phosphate, melamine pyrophosphate, a melamine salt of boron-polyphosphate, an ammonium salt of boron-polyphosphate, dicyandiamide pyrophosphate, triphenyl phosphite, ammonium dimethyl phosphate, fyroltex HP, melamine orthophosphate, ammonium urea phosphate, ammonium melamine phosphate, a urea salt of dimethyl methyl phosphonate, a melamine salt of dimethyl methyl phosphonate, a melamine salt of dimethyl hydrogen phosphite, polychlorinated biphenyls, a variety of alkyl diaryl phosphates and mixtures of monomeric chloroethyl phosphonates and high boiling phosphonates.

Metal hydroxide fire retardants include inorganic hydroxides, such as aluminum hydroxide, magnesium hydroxide, aluminum trihydroxide (ATH) and hydroxycarbonate.

Melamine-based fire retardants are a family of non-halogenated flame retardants that include three chemical groups: (a) melamine(2,4,6-triamino-1,3,5 triazine); (b) melamine derivatives (including salts with organic or inorganic acids, such as boric acid, cyanuric acid, phosphoric acid or pyro/poly-phosphoric acid); and (c) melamine homologues. Melamine derivatives include, for example, melamine cyanurate (a salt of melamine and cyanuric acid)), melamine-mono-phosphate (a salt of melamine and phosphoric acid), melamine pyrophosphate and melamine polyphosphate. Melamine homologues include melam (1,3,5-triazin-2,4,6-tri-amine-n-(4,6-diamino-1,3,5-triazine-2-yl), melem (2,5,8-triamino 1,3,4,6,7,9,9b-heptaazaphenalene) and melon (poly[8-amino-1,3,4,6,7,9,9b-heptaazaphenalene-2,5-diyl). Other melamine-based fire retardant compounds are set forth hereinabove.

Borate fire retardant compounds include zinc borate, borax (sodium borate), ammonium borate, and calcium borate. Zinc borate is a boron-based fire retardant having the chemical composition $xZnOyB_2O_3zH_2O$. Zinc borate can be used alone, or in conjunction with other chemical compounds, such as antimony oxide, alumina trihydrate, magnesium hydroxide or red phosphorous. It acts through zinc halide or zinc oxyhalide, which accelerate the decomposition of halogen sources and promote char formation.

Silicon-based materials include linear and branched chain-type silicone with (hydroxy or methoxy) or without (saturated hydrocarbons) functional reactive groups.

Phosphonic acid derivatives include phosphonic acid, ethylenediamine salt of phosphonic acid, tetrakis hydroxymethyl phosphonium chloride and n-methyl dimethylphosphono propionamide Examples of intumescent substances include, but are not limited to, ammonium polyphosphate, boric acid, chlorinated paraffin, DI-pentaerythritol, melamine, mono-ammonium phosphate, pentaerythritol, phosphate esters, polytetrafluoroethylene, tributoxyethyl phosphate, triethyl phosphate, tris (2-ethylhexyl) phosphonate, urea, xylene and zinc borate.

Examples of powdered metal containing flame retardant substances, which can be employed alone or in combination with other flame retardant substances, include, but are not limited to, magnesium oxide, magnesium chloride, talcum, alumina hydrate, zinc oxide, zinc borate, alumina trihydrate, alumina magnesium, calcium silicate, sodium silicate, zeolite, magnesium hydroxide, sodium carbonate, calcium carbonate, ammonium molybdate, iron oxide, copper oxide, zinc phosphate, zinc chloride, clay, sodium dihydrogen phosphate, tin, molybdenum and zinc.

Examples of fire retardant substances that can be applied to the fibers also include boric acid, boron oxide, calcium borate, alumina trihydrate (alumina hydroxide), alumina carbonate, hydrated aluminum, aluminum hydroxide, antimony oxide, antimony trioxide, antimony pentoxide, sodium antimonate, magnesium carbonate, potassium fluorotitanate, potassium fluorozirconate, zinc oxide, hunite-hydromagnesite, ammonium octamolybdate, ammonium bromide, ammonium sulfate, ammonium carbonate, ammonium oxylate, barium metaborate, molybdenum trioxide, zinc hydroxystannate, sodium tungstate, sodium antimonate, sodium stannate, sodium aluminate, sodium silicate, sodium bisulfate, ammonium borate, ammonium iodide, tin compounds, molybdic oxide, sodium antimonate, ammonium sulfamate, ammonium silicate, quaternary ammonium hydroxide, aluminum tryhydroxide, tetrabromobisphenol A, titanium compounds, zirconium compounds, other zinc compounds, such as zinc stannate and zinc hydroxy-stannate, dioxins, diethyl phosphite, methylamine boron-phosphate, cyanoquanidine, thiourea, ethyl urea, dicyandiamide and halogen-free phosphonic acid derivatives.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A mattress assembly comprising:
   at least one layer proximate to a sleeping surface of the mattress assembly spanning at least a portion of the length and/or width of the sleeping surface comprising:
   a two-ply preformed capsulate sheet comprising a plurality of cells, wherein each of the cells have a cellular volume greater than 1 $cm^3$; and
   a bulk amount of a phase change material free of microencapsulation consisting of the phase change material contained completely within at least a portion of the plurality of cells, wherein the two-ply preformed capsulate sheet is configured to provide the plurality of cells with the phase change material in an amount greater than about 100 grams per square foot of surface area of the preformed capsulate sheet.

2. The mattress assembly of claim 1, wherein the phase change material comprises one or more paraffinic hydrocarbons or bio-phase change materials having different melting points.

3. The mattress assembly of claim 1, further comprising a fire retardant within the cell.

4. The mattress assembly of claim 1, wherein the two-ply preformed capsulate sheet comprises recesses formed in a first sheet and a cover sheet coupled thereto to define the plurality of cells.

5. The mattress assembly of claim 1, wherein the phase change material comprises a mixture of phase change materials having different melting points.

6. The mattress assembly of claim 1, wherein the phase change material has a melting point in a range of about 22° C. to about 40° C.

7. The mattress assembly of claim 1, wherein the phase change material has a melting point in a range of about 26° C. to about 30° C.

8. The mattress assembly of claim 1, wherein the phase change material is in an amount effective to provide cooling or heating during a sleep cycle of at least one hour.

9. The mattress assembly of claim 1, wherein the plurality of cells comprises individual cells.

10. The mattress assembly of claim 1, wherein at least a portion of the plurality of cells are fluidly linked to one another.

11. The mattress assembly of claim 1, wherein the at least one layer underlies a portion of the sleeping surface of the mattress assembly.

12. The mattress assembly of claim 1, wherein the at least one layer is a topper layer.

13. The mattress assembly of claim 1, wherein the at least one layer proximate to the sleeping surface of the mattress assembly overlays a portion of the mattress assembly corresponding to a torso region of an end user.

14. The mattress assembly of claim 1, wherein the phase change material has a latent heat of at least about 40 J/g.

15. The mattress assembly of claim 1, wherein the two-ply preformed capsulate sheet comprising the plurality of cells and the phase change material within at least a portion of the plurality of cells further comprises foam within the cells, wherein the foam is saturated with the phase change material.

16. The mattress assembly of claim 1, wherein the two-ply preformed capsulate sheet is formed of a material selected to have mechanical properties to accommodate volume changes during phase change transitions and maintain thermal and tactile comfort during use thereof.

17. The mattress assembly of claim 1, wherein the wherein the two-ply preformed capsulate sheet comprises polyethylene.

18. A mattress assembly comprising:
a core layer;
at least one layer overlaying the core layer comprising a two-ply preformed capsulate sheet comprising a plurality of cells, and a bulk amount of phase change material free of microencapsulation consisting of the phase change material contained completely within at least a portion of the plurality of cells, wherein the two-ply preformed capsulate sheet is configured to provide the plurality of cells with the phase change material in an amount greater than about 100 grams per square foot of surface area of the preformed capsulate sheet, wherein each of the cells have a cellular volume greater than 1cm$^3$; and
a foam layer overlaying the at least one layer, wherein the at least one layer and the foam layer are proximate to a sleeping surface of the mattress assembly.

19. The mattress assembly of claim 18, wherein the phase change material comprises different melting points.

20. The mattress assembly of claim 18, wherein the foam layer comprises a viscoelastic layer.

21. The mattress assembly of claim 18, further comprising a fire retardant within the cell.

22. The mattress assembly of claim 18, wherein the two-ply preformed capsulate sheet comprises recesses formed in a carrier sheet and a cover sheet adhesively coupled thereto to define the plurality of cells.

23. The mattress assembly of claim 18, wherein the phase change material comprises a mixture of phase change materials having different melting points.

24. The mattress assembly of claim 18, wherein the phase change material has a melting point in a range of about 22° C. to about 40° C.

25. The mattress assembly of claim 18, wherein the phase change material has a melting point in a range of about 26° C. to about 30° C.

26. The mattress assembly of claim 18, wherein the phase change material is in an amount effective to provide cooling or heating during a sleep cycle of at least one hour.

27. The mattress assembly of claim 18, wherein the plurality of cells comprise individual cells.

28. The mattress assembly of claim 18, wherein at least a portion of the plurality of cells are fluidly linked to one another.

29. The mattress assembly of claim 18, wherein the at least one layer and the foam layer are components of a topper layer.

30. The mattress assembly of claim 18, wherein the at least one layer overlays a portion of the mattress assembly corresponding to a torso region of an end user.

31. The mattress assembly of claim 18, wherein the phase change material has a latent heat of at least about 40 J/g.

32. The mattress assembly of claim 18, wherein the at least one layer overlaying the core layer spans at least a portion of the length and/or width thereof.

33. The mattress assembly of claim 18, wherein the two-ply preformed capsulate sheet comprising the plurality of cells and the phase change material within at least a portion of the plurality of cells further comprises foam within the cells, wherein the foam is saturated with the phase change material.

34. The mattress assembly of claim 18, wherein the two-ply preformed capsulate sheet is formed of a material selected to have mechanical properties to accommodate volume changes during phase change transitions and maintain thermal and tactile comfort during use thereof.

35. The mattress assembly of claim 18, wherein the wherein the two-ply preformed capsulate sheet comprises polyethylene.

36. A mattress assembly comprising:
a first layer proximate to a sleeping surface of the mattress assembly spanning at least a portion of the length and/or width of the sleeping surface comprising a two-ply preformed capsulate sheet comprising a plurality of cells, and a bulk amount of phase phase change material free of microencapsulation within at least a portion of the plurality of cells, wherein the phase change layer in the first layer has a first transition temperature; and
at least one additional layer underlying the first layer, the at least one additional layer spanning at least a portion of the length and/or width of the sleeping surface comprises a two-ply preformed capsulate sheet comprising a plurality of cells; and a phase change material consisting of the phase change material contained completely within at least a portion of the plurality of cells, wherein the phase change layer in the at least one additional layer has a transition temperature different from the first transition temperature of the first layer, wherein the two-ply preformed capsulate sheet is configured to provide the plurality of cells with the phase change material in an amount greater than about 100 grams per square foot of surface area of the preformed capsulate sheet, wherein each of the cells have a cellular volume greater than 1 cm$^3$.

37. The mattress assembly of claim 36, wherein the first layer has a transition temperature greater than the at least one additional layer.

38. The mattress assembly of claim 36, wherein the first layer has a lower transition temperature than the one or more additional layers to define a temperature gradient.

39. The mattress assembly of claim 36, wherein the two ply preformed capsulate sheet comprises recesses formed in a carrier sheet and a cover sheet adhesively coupled thereto to define the plurality of cells.

40. The mattress assembly of claim 36, wherein the phase change materials in the first layer and the at least one additional layer have a melting point in a range of about 22° C. to about 40° C.

41. The mattress assembly of claim 36, wherein the phase change materials in the first layer and the at least one additional layer have a melting point in a range of about 26° C. to about 30° C.

42. The mattress assembly of claim 36, wherein the phase change material in the first layer and the at least one additional layer is in an amount effective to provide cooling or heating during a sleep cycle of at least one hour.

43. The mattress assembly of claim 36, wherein the plurality of cells comprise individual cells.

44. The mattress assembly of claim 36, wherein at least a portion of the plurality of cells are fluidly linked to one another.

45. The mattress assembly of claim 36, wherein the in the first layer and the at least one additional layer overlays a portion of the mattress assembly corresponding to a torso region of an end user.

46. The mattress assembly of claim 36, wherein the phase change material has a latent heat of at least about 40 J/g.

47. The mattress assembly of claim 36, wherein the at least one layer overlaying the core layer spans at least a portion of the length and/or width thereof.

48. The mattress assembly of claim 36, wherein the two-ply preformed capsulate sheet comprising the plurality of cells and the phase change material within at least a portion of the plurality of cells further comprises foam within the cells, wherein the foam is saturated with the phase change material.

49. The mattress assembly of claim 36, wherein the two-ply preformed capsulate sheet is formed of a material selected to have mechanical properties to accommodate volume changes during phase change transitions and maintain thermal and tactile comfort during use thereof.

50. The mattress assembly of claim 36, wherein the wherein the two-ply preformed capsulate sheet comprises polyethylene.

* * * * *